United States Patent
Chen

(10) Patent No.: US 12,234,200 B2
(45) Date of Patent: Feb. 25, 2025

(54) SYNTHETIC METHODS OF PREPARING ESKETAMINE

(71) Applicant: JANSSEN PHARMACEUTICA NV, Beerse (BE)

(72) Inventor: Cheng Yi Chen, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 586 days.

(21) Appl. No.: 17/603,603

(22) PCT Filed: Apr. 16, 2020

(86) PCT No.: PCT/EP2020/060737
§ 371 (c)(1),
(2) Date: Oct. 14, 2021

(87) PCT Pub. No.: WO2020/212510
PCT Pub. Date: Oct. 22, 2020

(65) Prior Publication Data
US 2022/0220062 A1    Jul. 14, 2022

Related U.S. Application Data

(60) Provisional application No. 62/834,636, filed on Apr. 16, 2019.

(51) Int. Cl.
| | | |
|---|---|---|
| *C07C 221/00* | (2006.01) | |
| *C07C 213/02* | (2006.01) | |
| *C07C 263/04* | (2006.01) | |
| *C07C 265/10* | (2006.01) | |
| *C07C 271/34* | (2006.01) | |

(52) U.S. Cl.
CPC .......... *C07C 221/00* (2013.01); *C07C 213/02* (2013.01); *C07C 263/04* (2013.01); *C07C 265/10* (2013.01); *C07C 271/34* (2013.01)

(58) Field of Classification Search
CPC ............ C07B 2200/05; C07B 2200/07; C07C 213/02; C07C 217/52; C07C 221/00; C07C 225/20; C07C 2601/14; C07C 2601/16; C07C 263/04; C07C 265/10; C07C 269/02; C07C 271/34
See application file for complete search history.

(56) References Cited

U.S. PATENT DOCUMENTS 6,040,479 A    3/2000  Steiner et al.
2021/0024461 A1  1/2021  Chen et al.

FOREIGN PATENT DOCUMENTS

WO    2016/180984 A1    11/2016
WO    WO2016180984    * 11/2016

OTHER PUBLICATIONS

Brunner., H., et al., "Asymmetric catalysis. Part 153: Metal-catalysed enantioselective α-ketol rearrangement," Tetrahedron: Asymmetry, vol. 14, Issue 15, Aug. 1, 2003, pp. 2177-2187.
Chen, C-Y., et al., "Enantioselective Syntheses of (S)-Ketamine and (S)-Norketamine," Organic Letters, vol. 21, No. 16, Aug. 8, 2019, pp. 6575-6578.
Fukumoto, "Antidepressant Potential of (R)-Ketamine in Rodent Models: Comparison with (S)-Ketamine," Journal of Pharmacology and Experimental Therapeutics. 2017;361:9-16.
Harmata, "Intramolecular 4+3 cycloadditions. A cyclohexenyl cation, its halogenated congener and a quasi-Favorskii rearrangement," Tetrahedron Lett. 2002, 43, 2347-2349.
Matthews, S.J., et al., "Ketamine for Treatment-Resistant Unipolar Depression", CNS Drugs, Mar. 1, 2012; 26(3): 189-204.
Nocquet, "The Allyl Cyanate/Isocyanate Rearrangement: An Efficient Tool for the Stereocontrolled Formation of Allylic C—N Bonds," Eur. J. Org. Chem. 2017, 1295-1307.
Noppers, "Absence of long-term analgesic effect from a short-term S-ketamine infusion on fibromyalgia pain: A randomized, prospective, double blind, active placebo-controlled trial", Eur, J. of Pain,. 2011, 942-949.
Paskalis, "Oral Administration of the NMDA Receptor Antagonist S-Ketamine as Add-on Therapy of Depression: A Case Series", Pharmacopsychiatry, 2010, pp. 33-35, vol. 40.
Paul, "Comparison of racemic ketamine and S-ketamine in treatment-resistant major depression: report of two cases", World J. of Bio. Psych., 2009, pp. 241-244, vol. 10(3).
Yoshimura, "Recent topics in catalytic asymmetric hydrogenation of ketones," Tet. Lett. 55, 2014, 3635-3640.
Yang, "R-ketamine: a rapid-onset and sustained antidepressant without psychotomimetic side effects," Transl Psychiatry. 2015;5:e632.
Zanos, "NMDAR inhibition-independent antidepressant actions of ketamine metabolites," Nature. 2016;533:481-486.
Zhang, "R (−)-ketamine shows greater potency and longer lasting antidepressant effects than S (+)-ketamine," Pharmacol Biochem Behav. 2014; 116:137-141.

* cited by examiner

*Primary Examiner* — Yevgeny Valenrod
*Assistant Examiner* — Blaine G Doletski
(74) *Attorney, Agent, or Firm* — BakerHostetler

(57) ABSTRACT

The present invention is directed to methods for the asymmetric synthesis of esketamine. The present invention is further directed to key intermediates in the asymmetric esketamine synthesis. In one embodiment, the invention is an asymmetric synthesis of esketamine comprising the conversion of (S)-2'-chloro-2-methoxy-3,4,5,6-5 tetrahydro-[1,1'-biphenyl]-3-yl carbamate to (S)-2'-chloro-1-isocyanato-6-methoxy-1,2,3,4-tetrahydro-1,1'-biphenyl.

9 Claims, No Drawings

SYNTHETIC METHODS OF PREPARING ESKETAMINE

CROSS-REFERENCE TO RELATED APPLICATIONS

This application is the National Stage Application of International Patent Application No. PCT/EP2020/060737, filed Apr. 16, 2020, which claims priority to U.S. Provisional Patent Application No. 62/834,636, filed Apr. 16, 2019, the disclosures of which are incorporated by reference herein.

FIELD OF THE INVENTION

The present invention is directed to pharmaceutical products, and to methods for the preparation of esketamine. The invention comprises asymmetric synthesis of esketamine, as well as key intermediates in the synthesis.

BACKGROUND OF THE INVENTION

Major Depressive Disorder is defined as the presence of one of more major depressive episodes that are not better accounted for psychotic disorder or bipolar disorder. A major depressive episode is characterized by meeting five or more of the following criteria during the same 2 week period which represent a change in functioning and include at least depressed/sad mood or loss of interest and pleasure, indifference or apathy, or irritability and is usually associated with a change in a number of neurovegetative functions, including sleep patterns, appetite and body weight, motor agitation or retardation, fatigue, impairment in concentration and decision making, feelings of shame or guilt, and thoughts of death or dying (Harrison's Principles of Internal Medicine, 2000). Symptoms of a depressive episode include depressed mood; markedly diminished interest or pleasure in all, or almost all, activities most of the day; weight loss when not dieting or weight gain, or decrease or increase in appetite nearly every day; insomnia or hypersomnia nearly every day; psychomotor agitation or retardation nearly every day; fatigue or loss of energy nearly every day; feelings of worthlessness or excessive or inappropriate guilt nearly every day; diminished ability to think or concentrate, or indecisiveness, nearly every day; recurrent thoughts of death, recurrent suicidal ideation without a specific plan, or a suicide attempt or a specific plan for committing suicide. Further, the symptoms cause clinically significant distress or impairment in social, occupational, or other important areas of functioning. (*Diagnostic and Statistical Manual of Mental Disorders*, 4$^{th}$ Edition, American Psychiatric Association, 1994)

Current treatment options for unipolar depression include monotherapy or combination therapy with various classes of drugs including mono-amine oxidase inhibitors (MAOI), tricyclic antidepressants (TCA), serotonin specific reuptake inhibitors (SSRI), serotonin noradrenergic reuptake inhibitors (SNRI), noradrenaline reuptake inhibitor (NRI), "natural products" (such as Kava-Kava, St. John's Wort), dietary supplement (such as s-adenosylmethionine) and others. More specifically, drugs used in the treatment of depression include, but are not limited to imipramine, amitriptyline, desipramine, nortriptyline, doxepin, protriptyline, trimipramine, maprotiline, amoxapine, trazodone, bupropion, clomipramine, fluoxetine, citalopram, sertraline, paroxetine, tianeptine, nefazodone, venlafaxine, desvenlafaxine, duloxetine, reboxetine, mirtazapine, phenelzine, tranylcypromine, and/or moclobemide. Several of these agents including, but not limited to, serotonin reuptake inhibitors are also used when depression and anxiety co-exist, such as in anxious depression.

In the clinic, 40-50% of depressed patients who are initially prescribed antidepressant therapy do not experience a timely remission of depression symptoms. This group typifies level 1 treatment-resistant depression, that is, a failure to demonstrate an "adequate" response to an "adequate" treatment trial (that is, sufficient intensity of treatment for sufficient duration). Moreover, about approximately 30% of depressed patients remain partially or totally treatment-resistant to at least two antidepressant treatments including combination treatments. Increasingly, treatment of treatment-resistant depression includes augmentation strategies including treatment with pharmacological agents such as, antipsychotics (such as quetiapine, aripiprazole, olanzapine, risperidone, and the like), lithium, carbamazepine, and triiodothyronine, and the like; adjunctive electroconvulsive therapy; adjunctive transcranial magnetic stimulation; etc.

Ketamine (a racemic mixture of the corresponding S- and R-enantiomers) is an NMDA receptor antagonist, with a wide range of effects in humans, including analgesia, anesthesia, hallucinations, dissociative effects, elevated blood pressure and bronchodilation. Ketamine is primarily used for the induction and maintenance of general anesthesia. Other uses include sedation in intensive care, analgesia (particularly in emergency medicine and treatment of bronchospasms. Ketamine has also been shown to be efficacious in the treatment of depression (particularly in those who have not responded to other anti-depressant treatment). In patients with major depressive disorders, ketamine has additionally been shown to produce a rapid antidepressant effect, acting within two hours.

Different enantiomers of ketamine have different potencies. For example, the S-ketamine enantiomer (or esketamine) has higher potency or affinity for the NMDA reception and thus potentially allowing for lower dosages; and is available for medical use under the brand name KETANEST S.

PAUL, R., et al., "Comparison of racemic ketamine and S-ketamine in treatment-resistant major depression: report of two cases", World J. of Bio. Psych., 2009, pp 241-244, Vol. 10(3) describe two cases studies in which patients with a history of recurrent major depression were treated with intravenous of ketamine and S-ketamine.

PASKALIS, G., et al., "Oral Administration of the NMDA Receptor Antagonist S-Ketamine as Add-on Therapy of Depression: A Case Series", Pharmacopsychiatry, 2010, pp 33-35, Vol. 40 present four case studies where depressed patients received 1.25 mg/kg oral S-ketamine as add-on to standard antidepressant therapy.

NOPPERS, I., et al., "Absence of long-term analgesic effect from a short-term S-ketamine infusion on fibromyalgia pain: A randomized, prospective, double blind, active placebo-controlled trial", Eur. J. of Pain., 2011, article in press, describe a trial assessing the analgesic efficacy of S-ketamine on fibromyalgia pain.

MATTHEWS, S. J., et al., "Ketamine for Treatment-Resistant Unipolar Depression", CNS Drugs, 2012, pp1-16, provide a review of emerging literature on ketamine and a review of the pharmacology of both ketamine and S-ketamine.

Research on the (R)-enantiomer has suggested that it might also have antidepressant activity: Zhang J C, Li S X, Hashimoto K. R (−)-ketamine shows greater potency and longer lasting antidepressant effects than S (+)-ketamine. Pharmacol Biochem Behav. 2014; 116:137-141, Yang C, Shirayama Y, Zhang J C, Ren Q, Yao W, Ma M, et al. R-ketamine: a rapid-onset and sustained antidepressant without psychotomimetic side effects. Transl Psychiatry. 2015; 5: e632, Zanos P, Moaddel R, Morris P J, Georgiou P, Fischell J, Elmer G I, et al. NMDAR inhibition-independent antidepressant actions of ketamine metabolites. Nature. 2016; 533:481-486, Fukumoto K, Toki H, Iijima M, Hashihayata T, Yamaguchi J-i, Hashimoto K, et al. Antidepressant Potential of (R)-Ketamine in Rodent Models: Comparison with (S)-Ketamine. Journal of Pharmacology and Experimental Therapeutics. 2017; 361:9-16.

Typical industrial production of ketamine involves preparation of racemic mixture, followed by chiral resolution in which the undesired enantiomer is discarded.

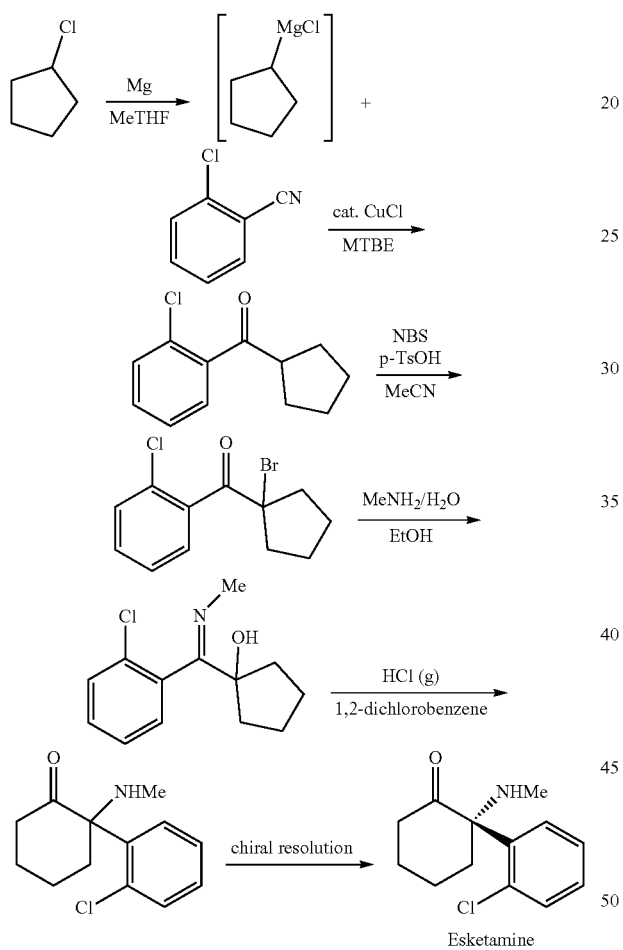

Esketamine

Therefore, since typical production of enantiomerically pure ketamine results in 50% waste; there remains a need to provide an effective asymmetric synthesis, which eliminates the waste and cost associated with preparing both desired and undesired enantiomers simultaneously.

SUMMARY OF THE INVENTION

The present invention is directed to methods for the asymmetric synthesis of esketamine.

The present invention is further directed to key intermediates in the asymmetric esketamine synthesis.

In one embodiment, the invention is an asymmetric synthesis of esketamine comprising the conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

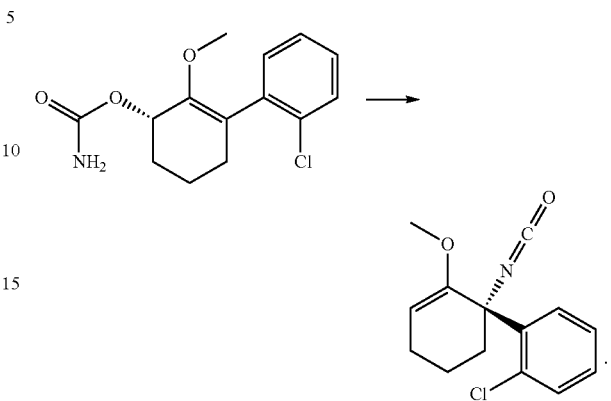

DETAILED DESCRIPTION OF THE INVENTION

The present invention is directed to methods for the asymmetric synthesis of esketamine.

In one embodiment, the invention is an asymmetric synthesis of esketamine, D3-esketamine, or (S)-norketamine comprising the conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

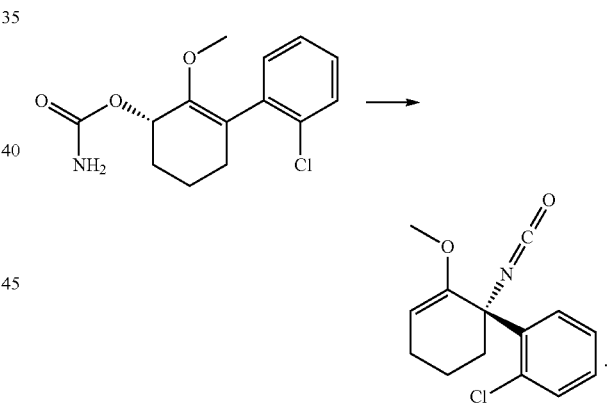

In another embodiment, the invention is an asymmetric synthesis of esketamine comprising the steps described below:

a) conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

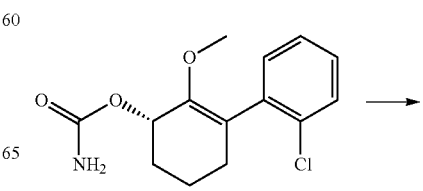

-continued

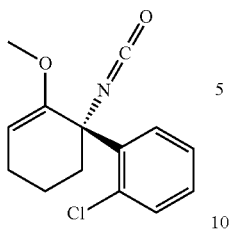

and b) reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

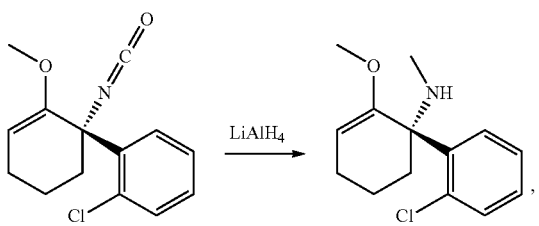

wherein said reduction is characterized by the use of lithium aluminum hydride.

In another embodiment, the invention is an asymmetric synthesis of esketamine comprising the steps described below:

a) conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

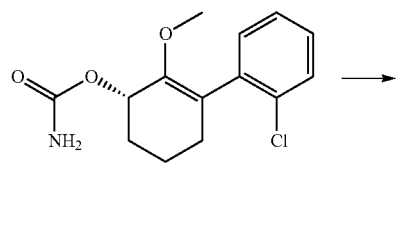

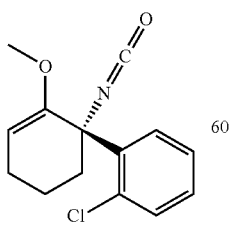

b) reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

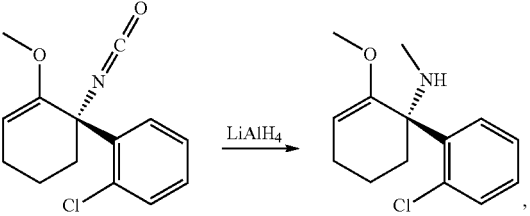

wherein said reduction is characterized by the use of lithium aluminum hydride, and c) deprotection of (S)-2'-chloro-6-methoxy-N-methyl-3,4-dihydro-[1,1'-biphenyl]-1(2H-amine to form esketamine

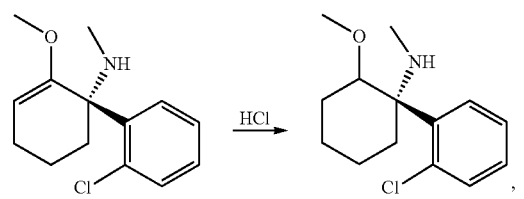 [SMILES: CN[C@]1(c2ccccc2Cl)CCCC=C1OC ; Cl ; CN[C@]1(c2ccccc2Cl)CCCCC1OC]

wherein said deprotection is characterized by the use of hydrochloric acid.

In another embodiment, the invention is an asymmetric synthesis of esketamine comprising the steps described below:

a) conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

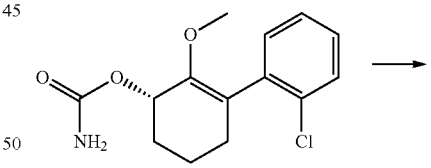

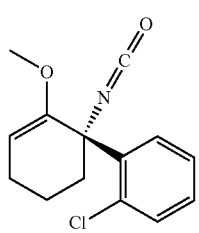

b) reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

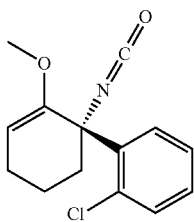 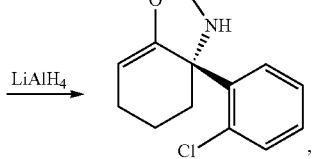

wherein said reduction is characterized by the use of lithium aluminum hydride, c) deprotection of (S)-2'-chloro-6-methoxy-N-methyl-3,4-dihydro-[1,1'-biphenyl]-1(2H)-amine to form esketamine

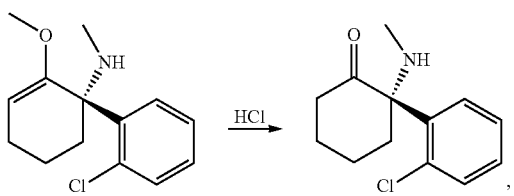 [SMILES: CN[C@]1(c2ccccc2Cl)CCCC=C1OC ; Cl ; CN[C@]1(c2ccccc2Cl)CCCCC1=O]

wherein said deprotection is characterized by the use of hydrochloric acid, and d) wherein the (S)-2'-chloro-2-methoxy-3,4,5,6-tetrahydro-[1,1'-biphenyl]-3-yl carbamate used in step a) is prepared by asymmetric reduction of 2'-chloro-2-methoxy-5,6-dihydro-[1,1'-biphenyl]-3(4H)-one:

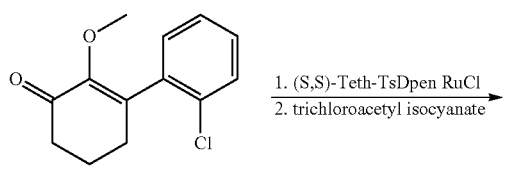

1. (S,S)-Teth-TsDpen RuCl
2. trichloroacetyl isocyanate

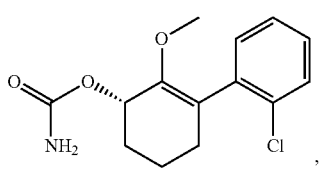

wherein said reduction is characterized by the use of (S,S)-Teth-TsDpen RuCl, followed by the use of trichloroacetyl isocyanate.

In another embodiment, the invention is an asymmetric synthesis of D3-esketamine comprising the steps described below:

a) conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

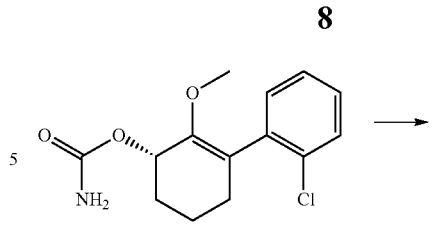

b) reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

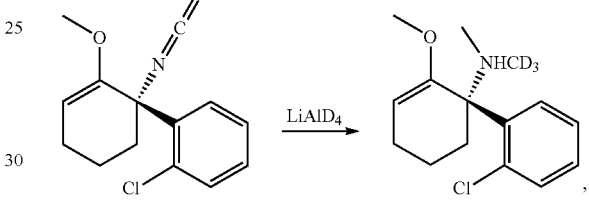

wherein said reduction is characterized by the use of lithium aluminum deuteride, and c) deprotection of (S)-2'-chloro-6-methoxy-N-methyl-3,4-dihydro-[1,1'-biphenyl](2-)-amine to form D3-esketamine

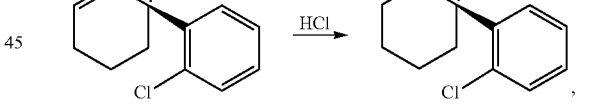

wherein said deprotection is characterized by the use of hydrochloric acid.

In another embodiment, the invention is an asymmetric synthesis of (S)-norketamine comprising the steps described below:

a) conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

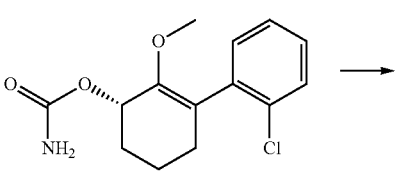

-continued

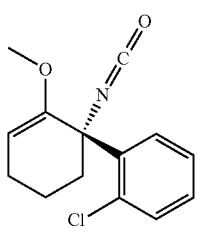

b) conversion of (S)-2'-chloro-1-isocyanato-6-methoxy-1,2,3,4-tetrahydro-1,1'-biphenyl to (S)-norketamine

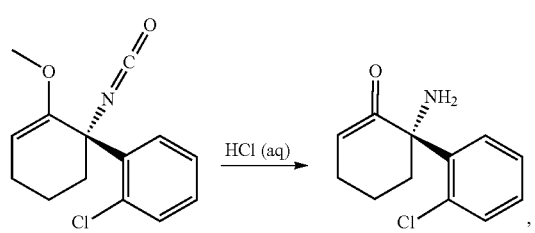

wherein said conversion is characterized by the use of hydrochloric acid.

Another embodiment of the invention is a compound which is (S)-2'-chloro-2-methoxy-3,4,5,6-tetrahydro-[1,1'-biphenyl]-3-yl carbamate

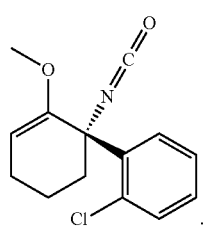

Another embodiment of the invention is a compound which is (S)-2'-chloro-1-isocyanato-6-methoxy-1,2,3,4-tetrahydro-1,1'-biphenyl In one embodiment, the invention is an asymmetric synthesis of esketamine, D3-esketamine, or (S)-norketamine comprising the conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

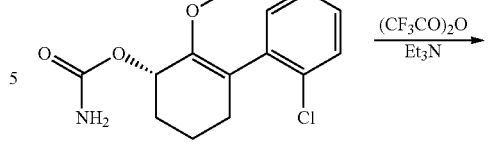

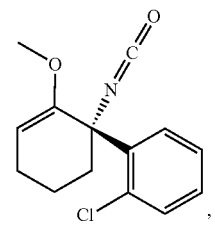

wherein said conversion is characterized by the use of trifluoroacetic anhydride and triethylamine.

In another embodiment, the invention is an asymmetric synthesis of esketamine comprising the steps described below:

a) conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

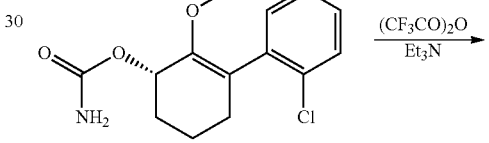

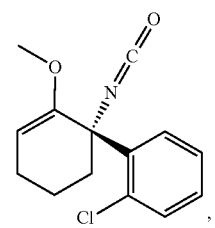

wherein said conversion is characterized by the use of trifluoroacetic anhydride and triethylamine, and b) reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

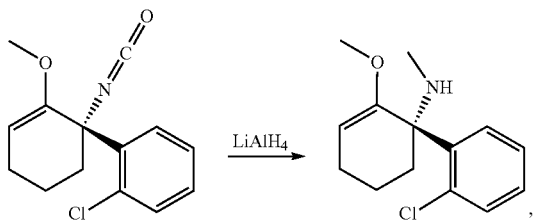

wherein said reduction is characterized by the use of lithium aluminum hydride.

In another embodiment, the invention is an asymmetric synthesis of esketamine comprising the steps described below:

a) conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

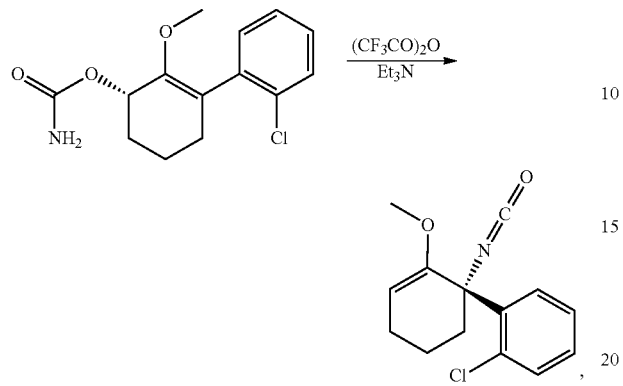

wherein said conversion is characterized by the use of trifluoroacetic anhydride and triethylamine, b) reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

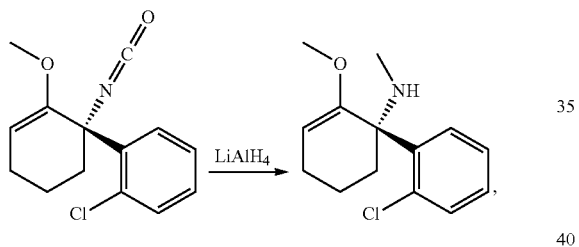

wherein said reduction is characterized by the use of lithium aluminum hydride, and c) deprotection of (S)-2'-chloro-6-methoxy-N-methyl-3,4-dihydro-[1,1'-biphenyl]-1(2H)-amine to form esketamine

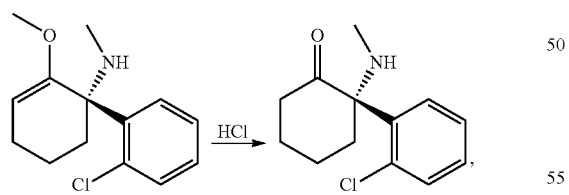

wherein said deprotection is characterized by the use of hydrochloric acid.

In another embodiment, the invention is an asymmetric synthesis of esketamine comprising the steps described below:

a) conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

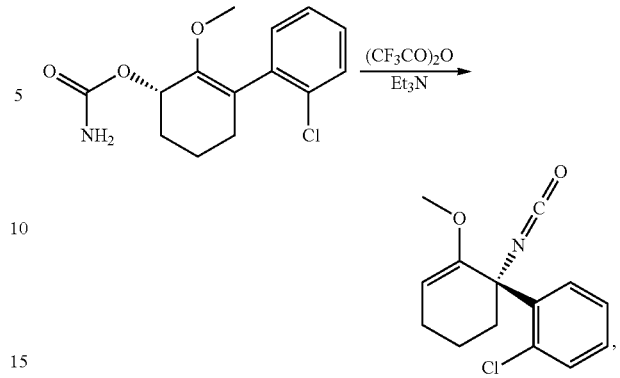

wherein said conversion is characterized by the use of trifluoroacetic anhydride and triethylamine, b) reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

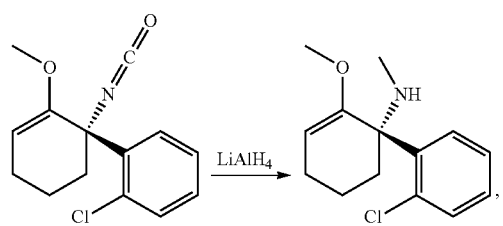

wherein said reduction is characterized by the use of lithium aluminum hydride, c) deprotection of (S)-2'-chloro-6-methoxy-N-methyl-3,4-dihydro-[1,1'-biphenyl]-1(2H)-amine to form esketamine

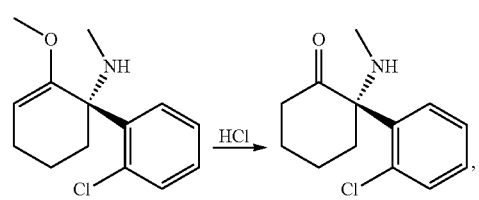 [SMILES: CN[C@]1(c2ccccc2Cl)CCCC=C1OC ; Cl ; CN[C@]1(c2ccccc2Cl)CCCCC1=O]

wherein said deprotection is characterized by the use of hydrochloric acid, and d) wherein the (S)-2'-chloro-2-methoxy-3,4,5,6-tetrahydro-[1,1'-biphenyl]-3-yl carbamate used in step a) is prepared by asymmetric reduction of 2'-chloro-2-methoxy-5,6-dihydro-[1,1'-biphenyl]-3(4H)-one:

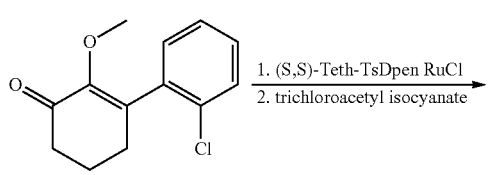

-continued

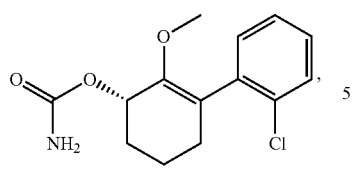

wherein said reduction is characterized by the use of (S,S)-Teth-TsDpen RuCl, followed by the use of trichloroacetyl isocyanate.

In another embodiment, the invention is an asymmetric synthesis of esketamine comprising the steps described below:

a) conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

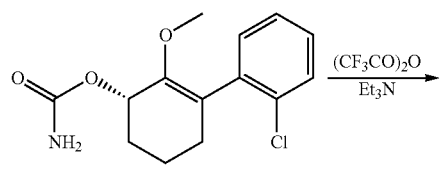

wherein said conversion is characterized by the use of trifluoroacetic anhydride and triethylamine, b) reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

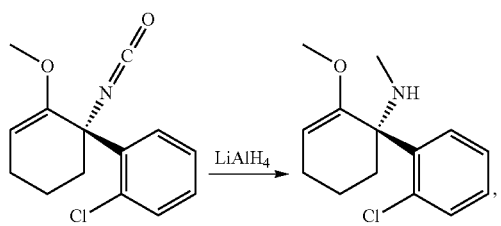

wherein said reduction is characterized by the use of lithium aluminum hydride, c) deprotection of (S)-2'-chloro-6-methoxy-N-methyl-3,4-dihydro-[1,1'-biphenyl]-1(2H)-amine to form esketamine

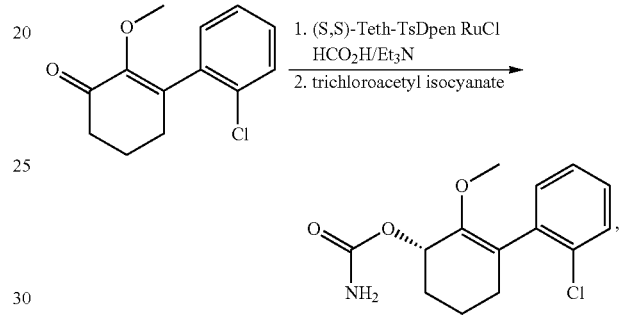

wherein said deprotection is characterized by the use of hydrochloric acid, and d) wherein the (S)-2'-chloro-2-methoxy-3,4,5,6-tetrahydro-[1,1'-biphenyl]-3-yl carbamate used in step a) is prepared by asymmetric reduction of 2'-chloro-2-methoxy-5,6-dihydro-[1,1'-biphenyl]-3(4H)-one:

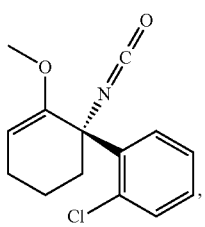

wherein said reduction is characterized by the use of (S,S)-Teth-TsDpen RuCl, followed by the use of trichloroacetyl isocyanate.

In another embodiment, the invention is an asymmetric synthesis of D3-esketamine comprising the steps described below:

a) conversion of (S)-2'-chloro-2-methoxy-3,4,5,6-tetrahydro-[j1,1'-biphenyl]-3-yl carbamate to (S)-2'-chloro-1-isocyanato-6-methoxy-1,2,3,4-tetrahydro-1,1'-biphenyl

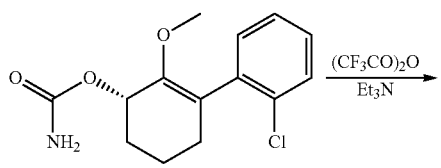

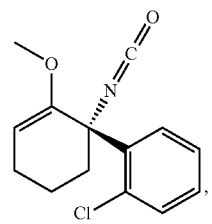

wherein said conversion is characterized by the use of trifluoroacetic anhydride and triethylamine, b) reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

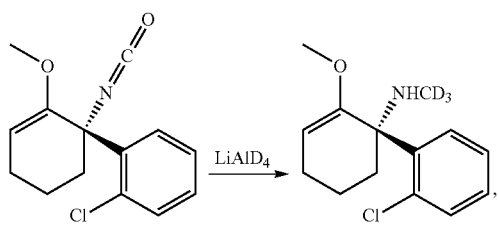

wherein said reduction is characterized by the use of lithium aluminum deuteride, and c) deprotection of (S)-2'-chloro-6-methoxy-N-methyl-3,4-dihydro-[1,1'-biphenyl]-1(2H)-amine to form D3-esketamine

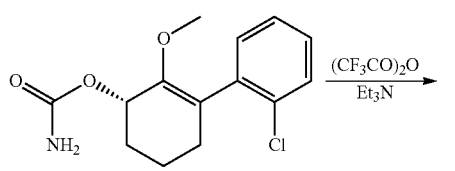

wherein said deprotection is characterized by the use of hydrochloric acid.

In another embodiment, the invention is an asymmetric synthesis of (S)-norketamine comprising the steps described below:

a) conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

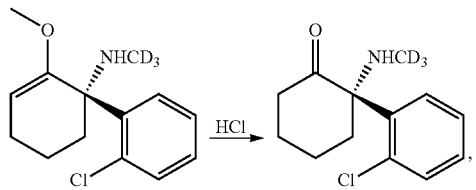

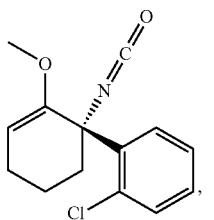

wherein said conversion is characterized by the use of trifluoroacetic anhydride and triethylamine, b) conversion of (S)-2'-chloro-1-isocyanato-6-methoxy-1,2,3,4-tetrahydro-1,1'-biphenyl to (S)-norketamine

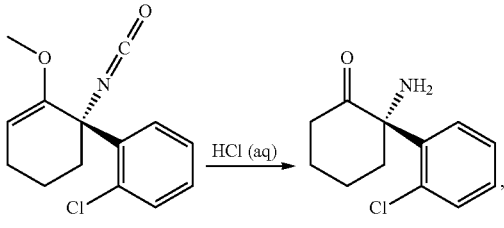

wherein said conversion is characterized by the use of hydrochloric acid.

The invention may be more fully appreciated by reference to the following description, including the following glossary of terms and the concluding examples.

As used herein, the terms "including", "containing" and "comprising" are used herein in their open, non-limiting sense.

Definitions

As used herein, the term "esketamine" shall mean the (S)-enantiomer of ketamine,

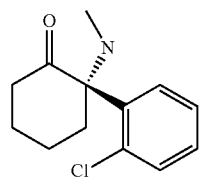 [SMILES: CN[C@]1(c2ccccc2Cl)CCCCC1=O]

also known as (S)-2-(2-chlorophenyl)-2-(methylamino)cyclohexanone.

As used herein, the term "D3-esketamine" shall mean the (S)-enantiomer of D3-ketamine,

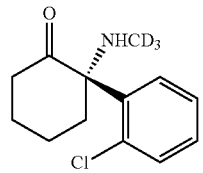

also known as (S)-2-(2-chlorophenyl)-2-((methyl-d3)amino)cyclohexan-1-one.

As used herein, the term "(S)-norketamine" shall mean the (S)-enantiomer of norketamine,

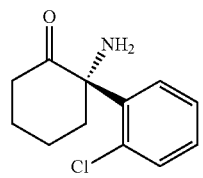 [SMILES: N[C@]1(c2ccccc2Cl)CCCCC1=O]

Also known as (S)-2-amino-2-(2-chlorophenyl)cyclohexan-1-one.

As used herein, the term "asymmetric synthesis", is a form of chemical synthesis wherein one enantiomer is formed in excess over another enantiomer.

As used herein, the term "(S,S)-Teth-TsDpen RuCl", is chloro[(S,S)-1,2-diphenyl-N1-(3-phenylpropyl)-N2-(p-toluenesulfonyl)-1,2-ethanediamine]ruthenium(II), for further clarity, (S,S)-Teth-TsDpen RuCl is

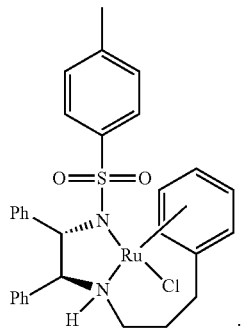

Where the compounds according to this invention have at least one stereocenter, they may exist as enantiomers. It is to be understood that all such enantiomers and mixtures thereof are encompassed within the scope of the present invention.

Where the reactions according to this invention give rise to an excess of at least one stereocenter, said reactions may be characterized as generating an enantiomeric excess of the resulting stereocenter in the product. It is to be understood that all such enantiomeric excesses are encompassed within the scope of the present invention. For example, an enantiomeric excess of at least 80% is considered to be within the scope of the invention. For additional example, an enantiomeric excess of at least 90% is considered to be within the scope of the invention. For additional example, an enantiomeric excess of at least 95% is considered to be within the scope of the invention. For additional example, an enantiomeric excess of at least 97% is considered to be within the scope of the invention.

Additionally, any formula given herein is intended to refer also to hydrates, solvates, and polymorphs of such compounds, and mixtures thereof, even if such forms are not listed explicitly.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, and chlorine, such as $^{2}H$, $^{3}H$, $^{11}C$, $^{13}C$, $^{14}C$, $^{15}N$, $^{18}O$, $^{17}O$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^{2}H$ or D) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Those skilled in the art will recognize that compounds and reagents used in the reactions of the invention may exist as salts. The invention contemplates the use of all salts of any compound used in a reaction exemplified herein.

Examples of salts include, without limitation, sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates. In some embodiments, the compound is the hydrochloride salt of esketamine.

When a compound or reagent used in a reaction of the invention contains a basic nitrogen, a salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

Exemplary reactions useful in methods of the invention will now be described by reference to the illustrative synthetic schemes for their general preparation below and the specific examples that follow. Those skilled in the art will recognize that reactions may be performed in any suitable solvent. Those skilled in the art will also recognize that, except where specifically limited, reactions may be performed at a wide range of temperatures. Unless otherwise specified, reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

ABBREVIATIONS

Herein and throughout the specification, the flowing abbreviations may be used.

| Abbreviation | Term |
|---|---|
| DCM | dichloromethane |
| DIPEA | diisopropyl ethylamine |
| EtOAc | ethyl acetate |
| EtOH | ethanol |
| Et$_3$N | triethylamine |
| h | hours |
| HOAc | acetic acid |
| HPLC | high-performance liquid chromatography |
| MeOH | methanol |
| OAc | acetate |
| PPh$_3$ | triphenylphosphine |
| TBAF | tetrabutylammonium fluoride |
| TFAA | trifluoroacetic acid anhydride |
| Tf$_2$O | trifluoromethane sulfonic anhydride |
| THF | tetrahydrofuran |
| TLC | thin layer chromatography |
| (S,S)-Teth-TsDpen RuCl | chloro[(S,S)-1,2-diphenyl-N1-(3-phenylpropyl)-N2-(p-toluenesulfonyl)-1,2-ethanediamine]ruthenium(II) |

NUMBERED EMBODIMENTS

1. An asymmetric synthesis of esketamine, D3-esketamine, or (S)-norketamine comprising
   conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

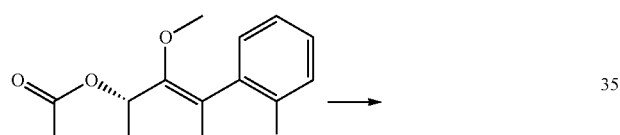

2. The asymmetric esketamine synthesis of numbered embodiment 1, further comprising reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

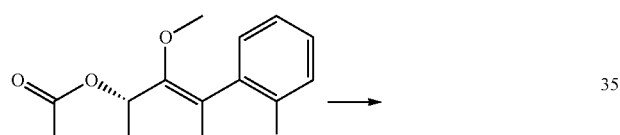

3. The asymmetric esketamine synthesis of numbered embodiment 1 or 2, further comprising reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2)-amine

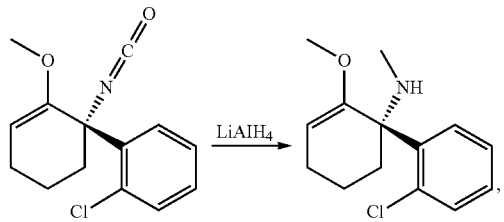

wherein said reduction is characterized by the use of lithium aluminum hydride.

4. The asymmetric synthesis of numbered embodiment 2 or 3, further comprising deprotection of (S)-2'-chloro-6-methoxy-N-methyl-3,4-dihydro-[1,1'-biphenyl]-1(2H)-amine to form esketamine

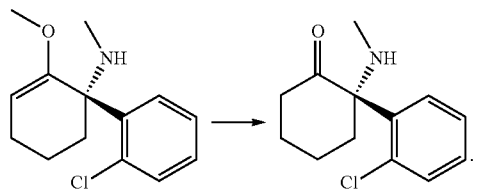 [SMILES: CN[C@]1(c2ccccc2Cl)CCCC=C1OC ; CN[C@]1(c2ccccc2Cl)CCCCC1=O]

5. The asymmetric synthesis of any one of numbered embodiments 2-4, further comprising deprotection of (S)-2'-chloro-6-methoxy-N-methyl-3,4-dihydro-[1,1'-biphenyl]-1(2H)-amine to form esketamine

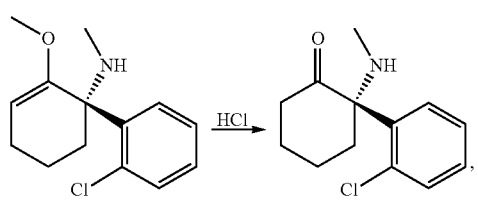 [SMILES: CN[C@]1(c2ccccc2Cl)CCCC=C1OC ; Cl ; CN[C@]1(c2ccccc2Cl)CCCCC1=O]

wherein said deprotection is characterized by the use of hydrochloric acid.

6. The asymmetric synthesis of any one of numbered embodiments 1-5, wherein the (S)-2'-chloro-2-methoxy-3,4,5,6-tetrahydro-[1,1'-biphenyl]-3-yl carbamate is prepared by asymmetric reduction of 2'-chloro-2-methoxy-5,6-dihydro-[1,1'-biphenyl]-3(4H)-one:

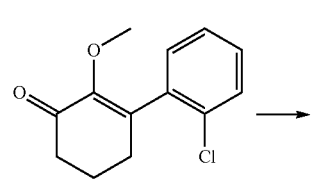

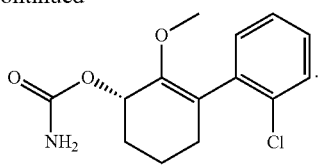

7. The asymmetric synthesis of any one of numbered embodiments 1-6, wherein the (S)-2'-chloro-2-methoxy-3,4,5,6-tetrahydro-[1,1'-biphenyl]-3-yl carbamate is prepared by asymmetric reduction of 2'-chloro-2-methoxy-5,6-dihydro-[1,1'-biphenyl]-3(4H)-one, followed by the use of trichloroacetyl isocyanate:

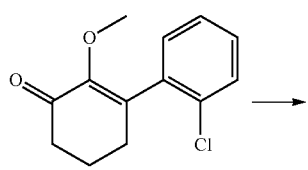 →

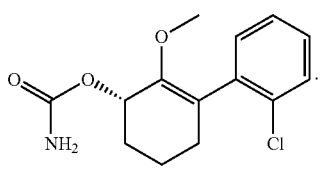

8. The asymmetric synthesis of any one of numbered embodiments 1-7, wherein the (S)-2'-chloro-2-methoxy-3,4,5,6-tetrahydro-[1,1'-biphenyl]-3-yl carbamate is prepared by asymmetric reduction of 2'-chloro-2-methoxy-5,6-dihydro-[1,1'-biphenyl]-3(4H)-one:

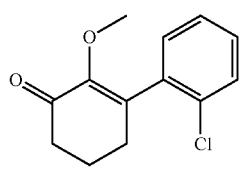

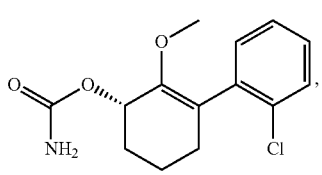

wherein said reduction is characterized by the use of (S,S)-Teth-TsDpen RuCl, followed by the use of trichloroacetyl isocyanate.

9. The asymmetric synthesis of any one of numbered embodiments 1-7, wherein the (S)-2'-chloro-2-methoxy-3,4,5,6-tetrahydro-[1,1'-biphenyl]-3-yl carbamate is prepared by asymmetric reduction of 2'-chloro-2-methoxy-5,6-dihydro-[1,1'-biphenyl]-3(4H)-one:

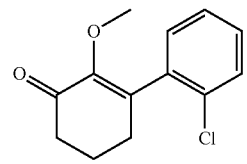

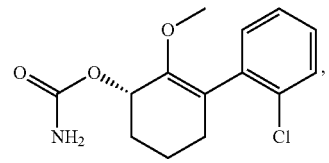

wherein said reduction is characterized by the use of (S,S)-Teth-TsDpen RuCl, followed by the use of trichloroacetyl isocyanate.

10. The asymmetric D3-esketamine synthesis of numbered embodiment 1, wherein the asymmetric synthesis of D3-esketamine further comprises the steps described below:

reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2I)-amine

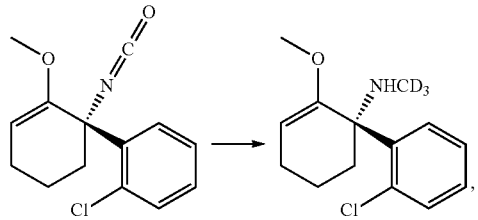

and deprotection of (S)-2'-chloro-6-methoxy-N-methyl-3,4-dihydro-[1,1'-biphenyl]-1(2H)-amine to form D3-esketamine

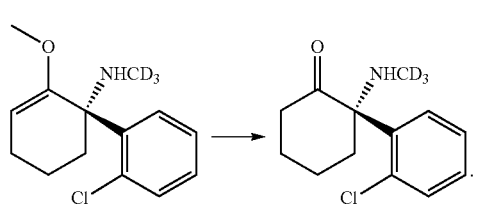

11. The asymmetric D3-esketamine synthesis of numbered embodiment 1 or 10, wherein the asymmetric synthesis of D3-esketamine further comprises the steps described below:

reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

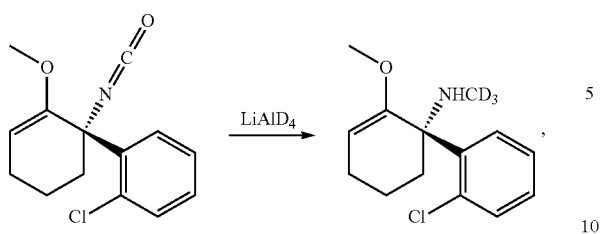

wherein said reduction is characterized by the use of lithium aluminum deuteride, and deprotection of (S)-2'-chloro-6-methoxy-N-methyl-3,4-dihydro-[1,1'-biphenyl]-1(2H)-amine to form D3-esketamine

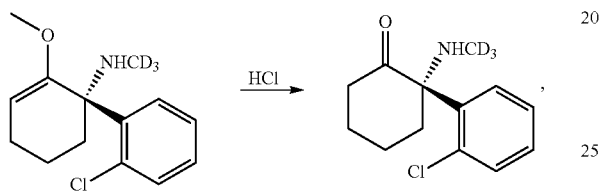

wherein said deprotection is characterized by the use of hydrochloric acid.

12. The asymmetric (S)-norketamine synthesis of numbered embodiment 1, wherein the asymmetric synthesis of (S)-norketamine further comprises conversion of (S)-2'-chloro-1-isocyanato-6-methoxy-1,2,3,4-tetrahydro-1,1'-biphenyl to (S)-norketamine

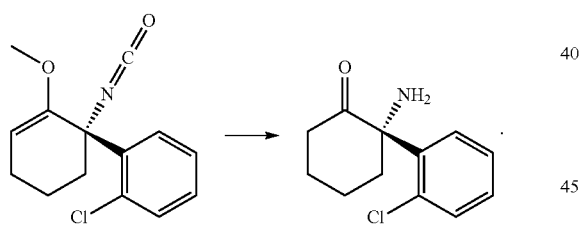

13. The asymmetric (S)-norketamine synthesis of numbered embodiment 1 or 12, wherein the asymmetric synthesis of (S)-norketamine further comprises conversion of (S)-2'-chloro-1-isocyanato-6-methoxy-1,2,3,4-tetrahydro-1,1'-biphenyl to (S)-norketamine

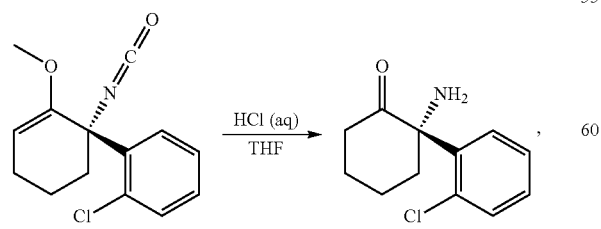

wherein said conversion is characterized by the use of hydrochloric acid.

14. A compound which is (S)-2'-chloro-2-methoxy-3,4,5,6-tetrahydro-[1,1'-biphenyl]-3-yl carbamate

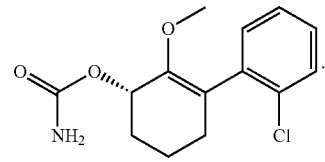

15. A compound which is (S)-2'-chloro-1-isocyanato-6-methoxy-1,2,3,4-tetrahydro-1,1'-biphenyl

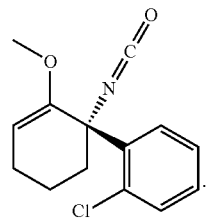 [SMILES: COC1=CCCC[C@]1(N=C=O)c1ccccc1Cl ; "."]

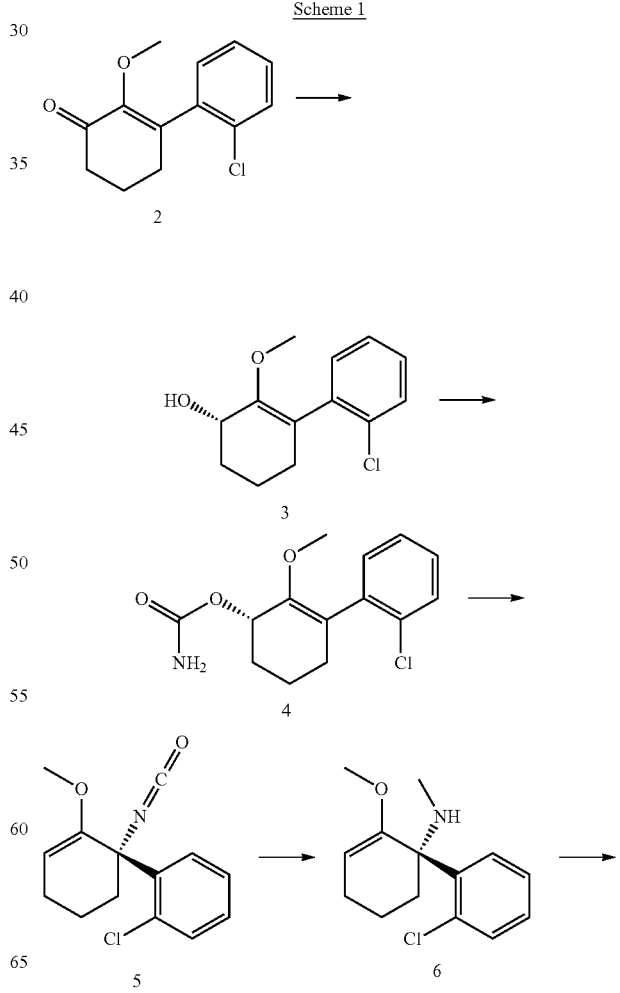

Scheme 1

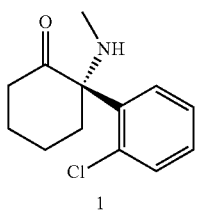

1

Scheme 1 Shows the Asymmetric Synthesis of Esketamine.

Achiral ketone 2 may be reduced to chiral alcohol 3 using a reductant, such as formic acid, and a chiral catalyst, for example (S,S)-Teth-TsDpen RuCl. Those skilled in the art will recognize that (R,R)-Teth-TsDpen RuCl may be used for the asymmetric synthesis of (R)-ketamine, D3-(R)-ketamine, or (R)-norketamine. Furthermore, those skilled in the art will recognize that asymmetric reduction of a ketone to a chiral alcohol may be accomplished by a number of reductants and a number of chiral catalysts, some of which are described by Masahiro Yoshimura, Shinji Tanaka, and Masato Kitamura in Recent topics in catalytic asymmetric hydrogenation of ketones; Tet. Lett. 55, 2014, 3635-3640 and references cited therein.

Alcohol 3 may be converted to carbamate 4 using trichloroacetyl isocyanate in a suitable solvent, such as but not limited to DCM.

Carbamate 4 rearrangement to isocyanate 5 may be performed under a variety of conditions, typically involving a dehydrating agent, a base, and low temperature. For example and without limitation, a carbamate to isocyanate rearrangement may be performed using TFAA and $Et_3N$ at 0° C., as described in example 3 below. Alternatively, the carbamate to isocyanate rearrangement may be performed using $Tf_2O$ and DIPEA at -78° C. Alternatively, the carbamate to isocyanate rearrangement may be performed using $PPh_3$ and $CBr_4$ with $Et_3N$ at -20° C. Many other combinations will be known to those skilled in the art, and the invention contemplates the use of all common means of carbamate-isocyanate rearrangement, including those described in Eur. J. Org. Chem. 2017, 1295-1307.

Conversion of isocyanate 5 to ketamine may be accomplished with a reductant, such as $LiAlH_4$, followed by deprotection with an acid such as HCl.

Scheme 2

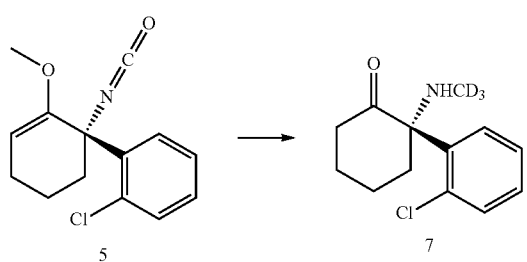

Scheme 2 Shows the Conversion of Isocyanate 5 to D3-Esketamine.

Conversion of isocyanate 5 to D3-ketamine may be accomplished with a deuterated reductant, such as LiAlD4, followed by deprotection with an acid such as HCl.

Scheme 3

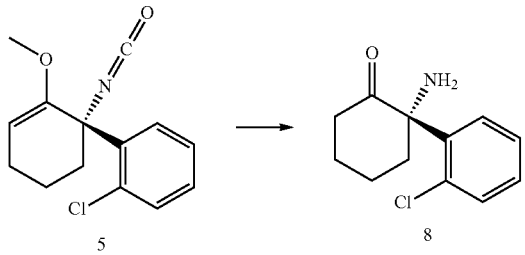

Scheme 3 Shows the Conversion of Isocyanate 5 to (S)-Norketamine.

Conversion of isocyanate 5 to norketamine may be accomplished with an acid such as HCl.

The following examples are for illustrative purposes only and are in no way meant to be limitation of the invention.

EXAMPLES

In obtaining the compounds described in the examples below and the corresponding analytical data, the following experimental and analytical protocols were followed unless otherwise indicated.

Unless otherwise stated, reaction mixtures were stirred at room temperature (rt) under a nitrogen atmosphere. Where mixtures, solutions, and extracts were "concentrated", they were typically concentrated under reduced pressure.

Normal-phase column chromatography was carried out with Sunasiachem silica gel (300-400 mesh), eluting with the indicated solvents.

High resolution mass spectra were recorded on Agilent 6030 TOF LC/MS machine using ESI (electrospray ionization). Calculated (calcd.) mass corresponds to the exact mass.

The optical rotation data were recorded on Autopol I-AP-S2 polarimeter. The melting point data were recorded on WRS-2A Micro Processor Melting-point Apparatus (uncalibrated).

$^1H$ NMR and $^{13}C$ NMR spectra were recorded on a Varian 400 NMR Spectrometer with chemical shifts reported in ppm relative to $Me_4Si$ for $^1H$ NMR and $CDCl_3$ or DMSO-d$^6$ for $^{13}C$ NMR, (multiplicity, coupling constant J in Hz, integration).

Chemical names were generated using ChemDraw Ultra 6.0.2 (CambridgeSoft Corp., Cambridge, MA) or ACD/Name Version 9 (Advanced Chemistry Development, Toronto, Ontario, Canada).

All commercially available reagents were used as received.

INTERMEDIATES

Synthesis of 2'-chloro-2-methoxy-5,6-dihydro-[1,1'-biphenyl]-3(4H)-one

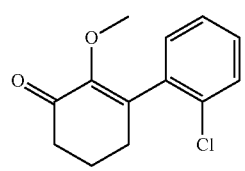

To a solution of crude 3-bromo-2-methoxycyclohex-2-en-1-one (prepared according to the procedure described in Harmata, M.; Bohnert, G.; Kurti, L.; Barnes, C. L. *Tetrahedron Lett.* 2002, 43, 2347) (1.31 g, 6.39 mmol, 1.0 eq.) in THF (20 mL) was added 2-chlorophenyl boric acid (1.30 g, 8.31 mmol, 1.3 eq.), $Pd(OAc)_2$ (72 mg, 0.319 mmol, 5 mol %), $PPh_3$ (168 mg, 0.639 mmol, 0.1 eq.) and a solution of $K_2CO_3$ (3.53 g, 25.6 mmol, 4 eq.) in $H_2O$ (12 mL) under N2 atmosphere. The biphasic mixture was stirred at 50° C. for 1 h, or until the bromo enone was consumed by TLC. The mixture was cooled to room temperature and diluted with EtOAc. The reaction was partitioned and extracted with EtOAc once. The combined organic layers were dried over $Na_2SO_4$, concentrated, and purified by silica gel column chromatography (eluted with EtOAc/heptane 1/5) to give the titled compound as a light yellow oil (853 mg, 88% yield). $^1$H NMR (400 MHz, $CDCl_3$) δ 7.39-7.32 (m, 1H), 7.24-7.16 (m, 2H), 7.14-7.07 (m, 1H), 3.42 (s, 3H), 2.56 (br s, 2H), 2.53 (t, J=6.7 Hz, 2H), 2.08-2.01 (m, 2H). $^{13}$C NMR (100 MHz, $CDCl_3$) δ 195.5, 149.2, 143.4, 137.1, 131.5, 129.7, 129.1, 129.3, 126.8, 59.9, 39.0, 31.0, 22.6. HRMS (ESI) calcd. for $C_{13}H_{14}ClO_2$ [M+H]$^+$: 237.0682, found: 237.0677.

Example 1

Synthesis of (S)-2'-chloro-2-methoxy-3,4,5,6-tetrahydro-[1,1'-biphenyl]-3-ol

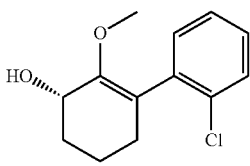 [SMILES: COC1=C(c2ccccc2Cl)CCC[C@@H]1O]

A solution of bromo enone 2 (3.0 g, 12.7 mmol, 1.0 eq.), (S,S)-Teth-TsDpen RuCl (7.9 mg, 0.013 mmol, 0.1 mol %) and $HCO_2H/Et_3N$ (2/3, v/v, 30 mL) was bubbled with $N_2$ at room temperature for 1 h. The mixture was heated to 80° C. and stirred for 2 h or until the enone was consumed by TLC. The reaction was cooled to room temperature and diluted with EtOAc and water. The organic layer was washed with HCl (3 N aq.) three times, and then washed with brine. The organic layer was dried with $Na_2SO_4$, concentrated, and purified by silica gel column chromatography (eluted with EtOAc/heptane 1/5) to give the alcohol 3 as a light yellow oil (2.8 g, 93% yield). $[α]D^{20}$=−89.2 (c 2.5, EtOH). $^1$H NMR (400 MHz, $CDCl_3$) δ 7.38-7.36 (m, 2H), 7.25-7.16 (m, 3H), 4.42 (s, 1H), 3.39 (s, 3H), 2.26-2.17 (br m, 3H), 1.93 (br s, 2H), 1.84-1.79 (m, 1H), 1.71-1.66 (m, 1H). $^{13}$C NMR (100 MHz, $CDCl_3$) δ 151.3, 139.1, 133.0, 130.6, 129.4, 128.1, 126.6, 119.6, 64.8, 57.7, 31.7, 30.4, 18.5. HRMS (ESI) calcd. for $C_{13}H_{16}ClO_2$ [M+H]$^+$: 239.0839, found: 239.0833.

Example 2a

Synthesis of (S)-2'-chloro-2-methoxy-3,4,5,6-tetrahydro-[1,1'-biphenyl]-3-yl carbamate

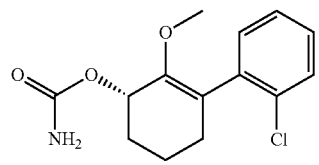 [SMILES: COC1=C(c2ccccc2Cl)CCC[C@@H]1OC(N)=O]

To a solution of 3 (1.5 g, 6.28 mmol, 1.0 eq.) in DCM (42 mL) at 0° C. was added trichloroacetyl isocyanate (2.37 g, 12.6 mmol, 2.0 eq.). The reaction solution was stirred at 0° C. for 15 min, warmed to room temperature, and stirred for an additional 15 min. After the allylic alcohol was consumed by TLC, the reaction solution was concentrated to dryness and diluted with MeOH (45 mL). The reaction was diluted with a solution of $K_2CO_3$ (6.95 g, 50.3 mmol, 8.0 eq.) in $H_2O$ (25 mL), stirred for 2 h, concentrated, and diluted with EtOAc and water. The reaction was partitioned and the aqueous layer was extracted with EtOAc twice. The combined organic layers were dried over $MgSO_4$, concentrated, and purified by silica gel column chromatography (eluted with MeOH/DCM 1/100) to obtain the carbamate 4 as a white solid (1.79 g, 100% yield). $[α]D^{20}$=−91.2 (c 2.5, EtOH). M. P. 181° C. $^1$H NMR (400 MHz, $CDCl_3$) δ 7.39-7.37 (m, 1H), 7.23-7.18 (m, 3H), 5.51 (s, 1H), 4.67 (s, 2H), 3.37 (s, 3H), 2.29 (br s, 2H), 2.10-2.04 (m, 1H), 1.92-1.85 (m, 1H), 1.82-1.68 (m, 2H). $^{13}$C NMR (100 MHz, DMSO-d$^6$) δ 156.7, 148.3, 139.3, 132.4, 131.1, 129.6, 128.9, 127.5, 64.9, 56.4, 30.0, 18.2. HRMS (ESI) calcd. for $C_{14}H_{17}ClNO_3$ [M+H]$^+$: 282.0897, found: 282.0891.

Example 2b—Alternative Prophetic Method

A suspension of NaOCN (2.72 g, 41.9 mmol, 2.0 eq.) in DCM (15 mL) is added a solution of 3 (5 g, 21.0 mmol, 1.0 eq.) in DCM (5 mL) at 0° C., followed by TFA (5.02 g, 44.0 mmol, 2.1 eq.). The reaction solution is stirred at 0° C. for 15 min, warmed to room temperature, and stirred for 12 h. After the allylic alcohol is consumed by TLC, the reaction is quenched with $H_2O$ (50 mL), partitioned, and the organic layer is extracted with DCM (50 mL) three times. The combined organics are dried over $MgSO_4$, concentrated, and purified on silica gel by column chromatography (eluted with MeOH/DCM 1/100), to give the carbamate 4.

Example 3

Synthesis of (S)-2'-chloro-1-isocyanato-6-methoxy-1,2,3,4-tetrahydro-1,1'-biphenyl

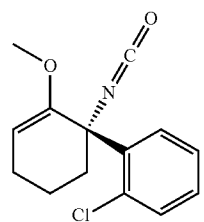 [SMILES: COC1=CCCC[C@]1(N=C=O)c1ccccc1Cl]

To a stirred solution of carbamate 4 (800 mg, 2.84 mmol, 1.0 eq.) and Et$_3$N (1.2 mL, 8.52 mmol, 3.0 eq.) in DCM (8 mL) at 0° C. was added TFAA (0.60 mL, 4.26 mmol, 1.5 eq.). After 2 h, the carbamate was consumed by TLC, quenched with H$_2$O, and diluted with DCM. The organic layer was dried over MgSO$_4$, concentrated under vacuum, and purified by column chromatography using basic silica gel (eluted with EtOAc/heptane 1/50) to obtain isocyanate 5 as a yellow oil (654 mg, 88% yield). [α]D$^{20}$=+7.1 (c 1.7, EtOH). $^1$H NMR (400 MHz, CDCl$_3$) δ 7.70 (dd, J=7.8, 1.6 Hz, 1H), 7.34 (dd, J=7.7, 1.5 Hz, 1H), 7.24 (dtd, J=24.0, 7.5, 1.6 Hz, 2H), 4.93 (t, J=4.2 Hz, 1H), 3.54 (s, 3H), 2.43 (ddd, J=13.6, 12.2, 3.3 Hz, 1H), 2.29-2.25 (m, 2H), 1.90 (ddd, J=13.5, 5.1, 2.9 Hz, 1H), 1.85-1.75 (m, 1H), 1.74-1.64 (m, 1H). $^{13}$C NMR (100 MHz, CDCl$_3$) δ 154.3, 139.9, 131.3, 131.2, 129.4, 129.3, 128.6, 126.7, 97.5, 65.7, 54.7, 37.6, 23.3, 19.4. HRMS (ESI) calcd. for C$_{14}$H$_{15}$ClNO$_2$ [M+H]$^+$: 264.0791, found: 264.0786.

Example 4

Synthesis of (S)-2'-chloro-6-methoxy-N-methyl-3,4-dihydro-[1,1'-biphenyl]-1(2H)-amine

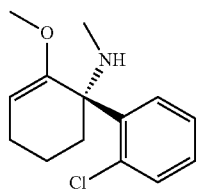 [SMILES: CN[C@]1(c2ccccc2Cl)CCCC=C1OC]

To a slurry of excess LiAlH$_4$ (115 mg, 3.03 mmol, 2.0 eq.) in THF (5 mL) was added a solution of isocyanate 5 (400 mg, 1.52 mmol, 1.0 eq.) in THF (5 mL). The reaction was heated to 70° C., stirred for 3 h, cooled to room temperature and quenched with a 30% NaOH aqueous solution (20 mL). The reaction was then heated to 90° C., stirred for 30 min, cooled to room temperature, and diluted with DCM. The reaction was partitioned and the aqueous layer was extracted with DCM once. The combined organic layers were dried over MgSO$_4$, concentrated, and purified with by silica gel column chromatography (eluted with EtOAc/heptane 1/3) to obtain methyl amine 6 as a light yellow oil (308 mg, 80% yield). [α]D$^{20}$=−80.5 (c 2.1, EtOH). $^1$H NMR (400 MHz, CDCl$_3$) δ 7.46 (dt, J=7.7, 1.7 Hz, 1H), 7.31 (dt, J=7.8, 1.5 Hz, 1H), 7.23-7.10 (m, 2H), 4.90 (t, J=3.9 Hz, 1H), 3.52 (s, 3H), 2.43-2.37 (m, 1H), 2.35 (s, 3H), 2.19-2.16 (m, 2H), 1.83-1.76 (m, 1H), 1.66-1.57 (m, 1H), 1.42-1.30 (m, 1H). $^{13}$C NMR (100 MHz, CDCl$_3$) δ 156.1, 141.2, 132.8, 131.53, 131.47, 127.8, 126.2, 97.5, 63.5, 53.8, 34.0, 31.4, 23.9, 19.3. HRMS (ESI) calcd. for C$_{14}$H$_{19}$ClNO [M+H]$^+$: 252.1155, found: 252.1105.

Example 5

Synthesis of Esketamine

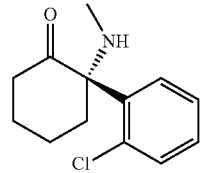 [SMILES: CN[C@]1(c2ccccc2Cl)CCCCC1=O]

To a solution of methyl amine 6 (230 mg, 0.914 mmol, 1.0 eq.) in THF (5 mL) was added an aqueous HCl solution (2 N, 5.5 mL, 11.0 mmol, 12 eq.). The stirred reaction was heated to 70° C. overnight, diluted with EtOAc and water, and partitioned. The aqueous layer was extracted with EtOAc once. The pH of the aqueous layer was adjusted to 10 with a 30% NaOH aqueous solution and extracted with EtOAc three times. The combined organics were washed with saturated aqueous NH$_4$Cl once, dried over MgSO$_4$, concentrated, and purified by silica gel column chromatography (eluted with EtOAc/heptane 1/3) to give esketamine 1 as an off-white solid (201 mg, 93% yield). The enantiomeric excess was determined to be 97.7% by chiral HPLC analysis. [α]D$^{20}$=−52.6 (c 2.4, EtOH). M. P. 120° C. $^1$H NMR (400 MHz, CDCl$_3$) δ 7.54 (dd, J=7.8, 1.4 Hz, 1H), 7.36 (dd, J=7.8, 1.4 Hz, 1H), 7.31 (td, J=7.6, 1.3 Hz, 1H), 7.23 (td, J=7.6, 1.6 Hz, 1H), 2.83-2.71 (m, 1H), 2.55-2.40 (m, 2H), 2.10 (s, 1H), 2.09 (s, 3H), 2.04-1.94 (m, 1H), 1.91-1.82 (m, 1H), 1.80-1.67 (m, 3H). $^{13}$C NMR (100 MHz, CDCl$_3$) δ 209.2, 137.8, 133.8, 131.2, 129.4, 128.7, 126.6, 70.2, 39.5, 38.6, 29.1, 28.1, 21.9. HRMS (ESI) calcd. for C$_{13}$H$_{16}$ClNO [M+H]$^+$: 238.0999, found: 238.0993.

Example 6

Synthesis of (S)-norketamine

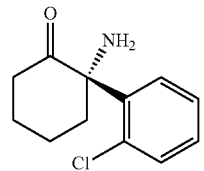 [SMILES: N[C@]1(c2ccccc2Cl)CCCCC1=O]

To a solution of isocyanate 5 (100 mg, 0.379 mmol, 1.0 eq., prepared as described in Example 3) in THF (1 mL) was added an aqueous HCl solution (3 N, 1.9 mL, 5.69 mmol, 15 eq.). The stirred solution was heated to 70° C. overnight. The reaction solution was then diluted with EtOAc and water. The reaction was partitioned, and the organic layer was extracted with EtOAc once. The pH of the aqueous layer was adjusted to 10 with a 30% NaOH aqueous solution, and the basic aqueous layer was extracted with EtOAc three times. The combined organics were washed with a saturated NH$_4$Cl aqueous solution once, dried over MgSO$_4$, concentrated, and purified by silica gel column chromatography (eluted with EtOAc/heptane 1/3) to give (S)-norketamine (62 mg, 74% yield) as a light yellow oil. $^1$H NMR (400 MHz, CDCl$_3$) δ 7.68 (d, J=7.8 Hz, 1H), 7.40-7.30 (m, 2H), 7.27-7.23 (m, 1H), 2.80-2.71 (m, 1H), 2.60-2.55 (m, 1H), 2.52-2.40 (m, 1H), 2.06-2.01 (m, 1H), 1.91 (s, 2H), 1.85-1.75 (m, 3H), 1.70-1.64 (m, 1H). $^{13}$C NMR (100 MHz, CDCl$_3$) δ 212.9, 140.4, 133.1, 131.1, 129.0, 128.4, 127.2, 66.5, 41.4, 39.1, 28.5, 22.2.

Example 7

Synthesis of D3-esketamine

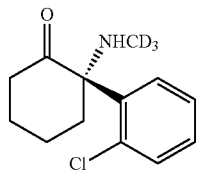

To a slurry of excess LiAlD4 (158 mg, 3.80 mmol, 2.0 eq.) in THF (5 mL) was added a solution of isocyanate 5 (500 mg, 1.90 mmol, 1.0 eq., prepared as described in Example 3) in THF (5 mL). The reaction suspension was heated to 70° C., stirred for 3 h, cooled to room temperature, and quenched with a 30% NaOH aqueous solution (20 mL). The slurry was heated to 90° C., stirred for 30 min, cooled to room temperature, and diluted with DCM. The reaction was partitioned, and the organic layer was extracted with DCM once. The combined organics were dried over MgSO$_4$, concentrated, diluted with THF (6 mL), and used for the next step without purification. The THF solution was treated with an aqueous HCl solution (4 N, 6 mL, 23.6 mmol, 12 eq.), heated to 70° C., and stirred overnight. The reaction solution was diluted with EtOAc and water. The reaction was partitioned, and the organic layer was extracted with EtOAc once. The pH of the aqueous layer was adjusted to 10 with a 30% NaOH aqueous solution, and the basic aqueous layer was extracted with EtOAc three times. The combined organics were washed with a saturated NH$_4$Cl aqueous solution once, dried over MgSO$_4$, concentrated, and purified by silica gel column chromatography (eluted with EtOAc/heptane 1/5 to 1/1) to give D3-ketamine (264 mg, 58% yield for 2 steps) as an off-white solid. $^1$H NMR (400 MHz, CDCl$_3$) δ 7.68 (d, J=7.8 Hz, 1H), 7.40-7.30 (m, 2H), 7.27-7.23 (m, 1H), 2.80-2.71 (m, 1H), 2.60-2.55 (m, 1H), 2.52-2.40 (m, 1H), 2.06-2.01 (m, 1H), 1.91 (s, 2H), 1.85-1.75 (m, 3H), 1.70-1.64 (m, 1H). $^{13}$C NMR (100 MHz, CDCl$_3$) δ 212.9, 140.4, 133.1, 131.1, 129.0, 128.4, 127.2, 66.5, 41.4, 39.1, 28.5, 22.2.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

I claim:

1. An asymmetric synthesis of esketamine, D3-esketamine, or (S)-norketamine comprising
    conversion of (S)-2'-chloro-2-methoxy-3,4,5,6-tetrahydro-[1,1'-biphenyl]-3-yl carbamate to (S)-2'-chloro-1-isocyanato-6-methoxy-1,2,3,4-tetrahydro-1,1'-biphenyl

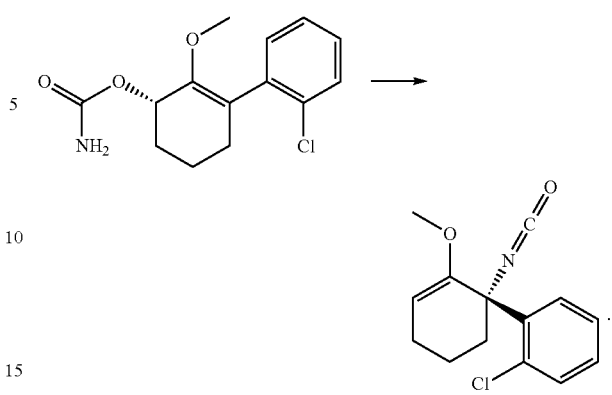

2. The asymmetric esketamine synthesis of claim 1, further comprising reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

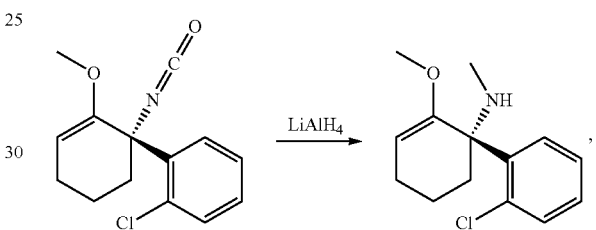

wherein said reduction is characterized by the use of lithium aluminum hydride.

3. The asymmetric synthesis of claim 2, further comprising deprotection of (S)-2'-chloro-6-methoxy-N-methyl-3,4-dihydro-[1,1'-biphenyl]-1(2H)-amine to form esketamine

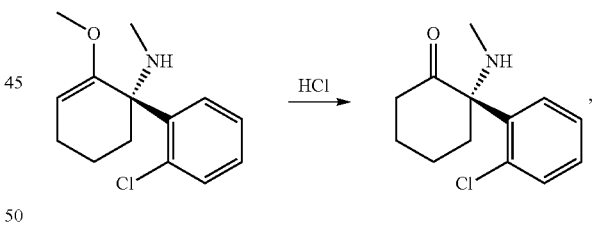

wherein said deprotection is characterized by the use of hydrochloric acid.

4. The asymmetric synthesis of claim 3, wherein the (S)-2'-chloro-2-methoxy-3,4,5,6-tetrahydro-[1,1'-biphenyl]-3-yl carbamate is prepared by asymmetric reduction of 2'-chloro-2-methoxy-5,6-dihydro-[1,1'-biphenyl]-3(4H)-one:

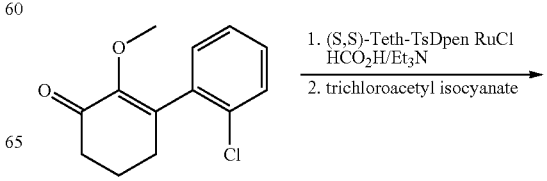

-continued

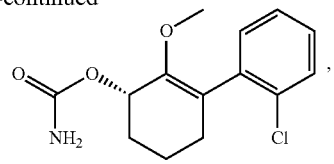, wherein said reduction is characterized by the use of (S,S)-Teth-TsDpen RuCl, followed by the use of trichloroacetyl isocyanate.

5. The asymmetric synthesis of claim 3, wherein the (S)-2'-chloro-2-methoxy-3,4,5,6-tetrahydro-[1,1'-biphenyl]-3-yl carbamate is prepared by asymmetric reduction of 2'-chloro-2-methoxy-5,6-dihydro-[1,1'-biphenyl]-3(4H)-one:

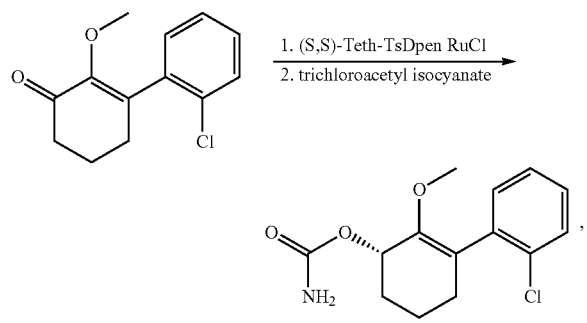

wherein said reduction is characterized by the use of (S,S)-Teth-TsDpen RuCl, followed by the use of trichloroacetyl isocyanate.

6. The asymmetric D3-esketamine synthesis of claim 1, wherein the asymmetric synthesis of D3-esketamine further comprises the steps described below:
    reduction of (S)-2'-chloro-1-isocyanato-6-methoxy-1,2,3,4-tetrahydro-1,1'-biphenyl to form (S)-2'-chloro-6-methoxy-N-methyl-3,4-dihydro-[1,1'-biphenyl]-1(2H)-amine

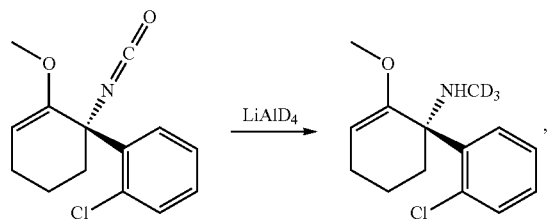

wherein said reduction is characterized by the use of lithium aluminum deuteride, and
    deprotection of (S)-2'-chloro-6-methoxy-N-methyl-3,4-dihydro-[1,1'-biphenyl]-1(2H)-amine to form D3-esketamine

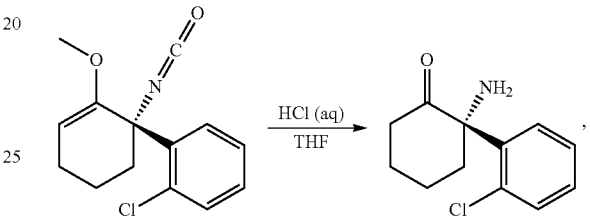

wherein said deprotection is characterized by the use of hydrochloric acid.

7. The asymmetric (S)-norketamine synthesis of claim 1, wherein the asymmetric synthesis of (S)-norketamine further comprises conversion of (S)-2'-chloro-1-isocyanato-6-methoxy-1,2,3,4-tetrahydro-1,1'-biphenyl to (S)-norketamine

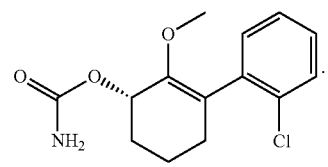

wherein said conversion is characterized by the use of hydrochloric acid.

8. A compound which is (S)-2'-chloro-2-methoxy-3,4,5,6-tetrahydro-[1,1'-biphenyl]-3-yl carbamate

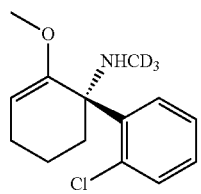.

9. A compound which is (S)-2'-chloro-1-isocyanato-6-methoxy-1,2,3,4-tetrahydro-1,1'-biphenyl

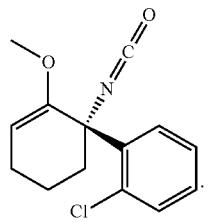.

* * * * *